United States Patent
Oyler

(10) Patent No.: US 8,697,418 B1
(45) Date of Patent: Apr. 15, 2014

(54) USE OF MIXED SPECIES FOR RAPID GROWTH OF AQUATIC BIOMASS

(75) Inventor: James R. Oyler, Salt Lake City, UT (US)

(73) Assignee: Genifuel Corporation, Salt Lake City, UT (US)

( * ) Notice: Subject to any disclaimer, the term of this patent is extended or adjusted under 35 U.S.C. 154(b) by 196 days.

(21) Appl. No.: 12/850,571

(22) Filed: Aug. 4, 2010

Related U.S. Application Data

(60) Provisional application No. 61/231,152, filed on Aug. 4, 2009.

(51) Int. Cl.
*C12N 1/00* (2006.01)
*C12N 1/12* (2006.01)

(52) U.S. Cl.
USPC ........................................ 435/243; 435/257.1

(58) Field of Classification Search
USPC .............................................. 435/243, 257.1
See application file for complete search history.

(56) References Cited

PUBLICATIONS

Acs et al. (Short-term colonization sequence of periphyton on glass slides in a large river (River Danube, near Budapest) Algological Studies. 2000. 100: 135-156).*
Makk et al. (Investigations on the Danube gravel-biofilm diatom-associated bacterial communities. Biologia. (2003) 58(4): 729-742).*
Warda et al. (Characterization of the autotrophic component in periphyton upon typha angustifolia detritus in a freshwater wetland. Eastern Michigan University Digital Commons. 2002. p. i-75).*
Laamanen et al. (Diversity of Toxic and Nontoxic Nodularia Isolates (Cyanobacteria) and Filaments from the Baltic Sea. Applied and Environmental Microbiology, 2001, p. 4638-4647).*
Triska et al. (Dentrification Associated with Periphyton Communities. Applied and Environmental Microbiology. 1981. vol. 42(4): 745-748).*
Marshall et al. (Effect of Marine Bacterial Isolates on the Growth and Morphology of Axenic Plantlets of the Green Alga Ulva linza. 2006. Microbial Ecology; 52: 302-310).*
Fonseca et al. (Periphytic Cyanobacteria in different environments from the upper Paraná river floodplain, Brazil. Acta Limnol. Bras. 2007. 19(1):53-65).*
Mueller et al. (Analysis of a marine phototrophic biofilm by confocal laser scanning microscopy using the new image quantification software PHLIP. BMC Ecology (2006) 6:1-15.*

* cited by examiner

*Primary Examiner* — Karen Cochrane Carlson
*Assistant Examiner* — Natalie Moss
(74) *Attorney, Agent, or Firm* — Thorpe North & Western LLP

(57) ABSTRACT

The present invention provides aquatic biomass having enhanced growth and methods for selecting and growing a mix of aquatic organisms to maximize production of such a biomass. In one aspect, for example, a method of enhancing aquatic biomass growth is provided. Such a method can include preselecting at least two organisms selected from the group consisting of an algae mixture, a cyanobacteria mixture, and a diatom mixture, combining the at least two organisms at a growth enhancing ratio in a growth environment, and growing the at least two organisms as an aquatic biomass under environmental conditions in the growth environment that further enhance biomass growth, wherein the aquatic biomass growth is synergistic.

18 Claims, 1 Drawing Sheet

USE OF MIXED SPECIES FOR RAPID GROWTH OF AQUATIC BIOMASS

PRIORITY DATA

This application claims the benefit of U.S. Patent Application Ser. No. 61/231,152, filed on Aug. 4, 2009, which is incorporated herein by reference.

FIELD OF THE INVENTION

The present invention relates to the use of a mix of species from different taxonomical groups to achieve faster growth and higher yield of aquatic biomass for use in the production of biofuels.

BACKGROUND OF THE INVENTION

In the field of biofuels production, one method of producing usable fuels is to gasify biomass. Gasification can be accomplished by various methods, including pyrolysis, catalytic hydrothermal gasification, and anaerobic digestion. Regardless of the method of gasification, the ability to produce the biomass feedstock as cheaply and quickly as possible is critical to achieve the highest possible production of the output fuel. In addition, it is desirable that the production of feedstock should not use excessive resources such as nutrients (fertilizer), water, or land used for food production.

Aquatic species have a number of advantages relative to these criteria. Ponds or troughs to grow aquatic organisms can be located on arid or infertile land, the amount of water can be reduced by using shallow depths, and nutrients in the water are not lost by leaching into the soil with a properly constructed containment. In addition, the use of catalytic hydrothermal gasification in particular requires that the biomass be processed in the form of a wet slurry. Since aquatic species are soft and wet, they are ideal for this process, and thus avoid the need for expensive grinding or drying of woody or other rigid terrestrial materials.

When other factors such as temperature, water, and nutrients are controlled, the amount of biomass produced per unit of area and per unit of time depends on the growing efficiency of the particular species, and ultimately on the quantum efficiency of converting photons from sunlight into stored energy via photosynthesis.

SUMMARY OF THE INVENTION

The present invention provides aquatic biomass having enhanced growth and methods for selecting and growing a mix of aquatic organisms to maximize production of such a biomass. In one aspect, for example, a method of enhancing aquatic biomass growth is provided. Such a method can include preselecting at least two organisms selected from the group consisting of an algae mixture, a cyanobacteria mixture, and a diatom mixture, combining the at least two organisms at a growth enhancing ratio in a growth environment, and growing the at least two organisms as an aquatic biomass under environmental conditions in the growth environment that further enhance biomass growth. In some aspects, the aquatic biomass growth is synergistic. In one aspect, the at least two organisms further includes three organisms including at least one alga, at least one cyanobacterium, and at least one diatom. In another aspect, at least one of the organisms includes at least two species of organisms.

Numerous organisms and species of organisms are contemplated for growth as an aquatic biomass. It should be noted that organisms and species are selected such that they provide a benefit to the growth of the aquatic biomass that often functions to enhance the overall growth. For example, in one aspect one of the at least two organisms can be an alga that is filamentary. In another aspect, one of the at least two organisms can be a cyanobacterium that is filamentary.

In another aspect, a method of enhancing growth of an aquatic biomass can include preselecting a combination of photosynthetic biomass constituents that provide the aquatic biomass with buoyancy control, a photoabsorption capacity in a spectrum of 350 nm to 750 nm in wavelength that is about 30% to about 70% greater than any single biomass constituent, and a degree of photoinhibition in the 350 nm to 750 nm wavelength spectrum that is about 30% to about 70% less than a single biomass constituent. The method can further include combining the photosynthetic biomass constituents at a growth accelerating ratio and growing the combination of photosynthetic biomass constituents in natural sunlight and at a temperature range of from about 10° C. to about 35° C. In some aspects, the growth achieved by such a combination may be synergistic.

The present invention also provides aquatic biomasses with accelerated growth capacity. Such a biomass can include a preselected combination of photosynthetic biomass constituents that provide the aquatic biomass with buoyancy control, a photoabsorption capacity in a spectrum of 350 nm to 750 nm in wavelength that is about 30% to about 70% greater than a single biomass constituent, and a degree of photoinhibition in the 350 nm to 750 nm wavelength spectrum that is about 30% to about 70% less than a single biomass constituent. In a more specific aspect, the biomass constituents include at least two organisms selected from the group consisting of an algae mixture, a cyanobacteria mixture, and a diatom mixture. In a further specific aspect, at least one of the organisms includes at least two species of organisms. In yet a further specific aspect, the at least two organisms includes three organisms including at least one alga, at least one cyanobacterium, and at least one diatom.

DETAILED DESCRIPTION OF THE INVENTION

Figure 1:
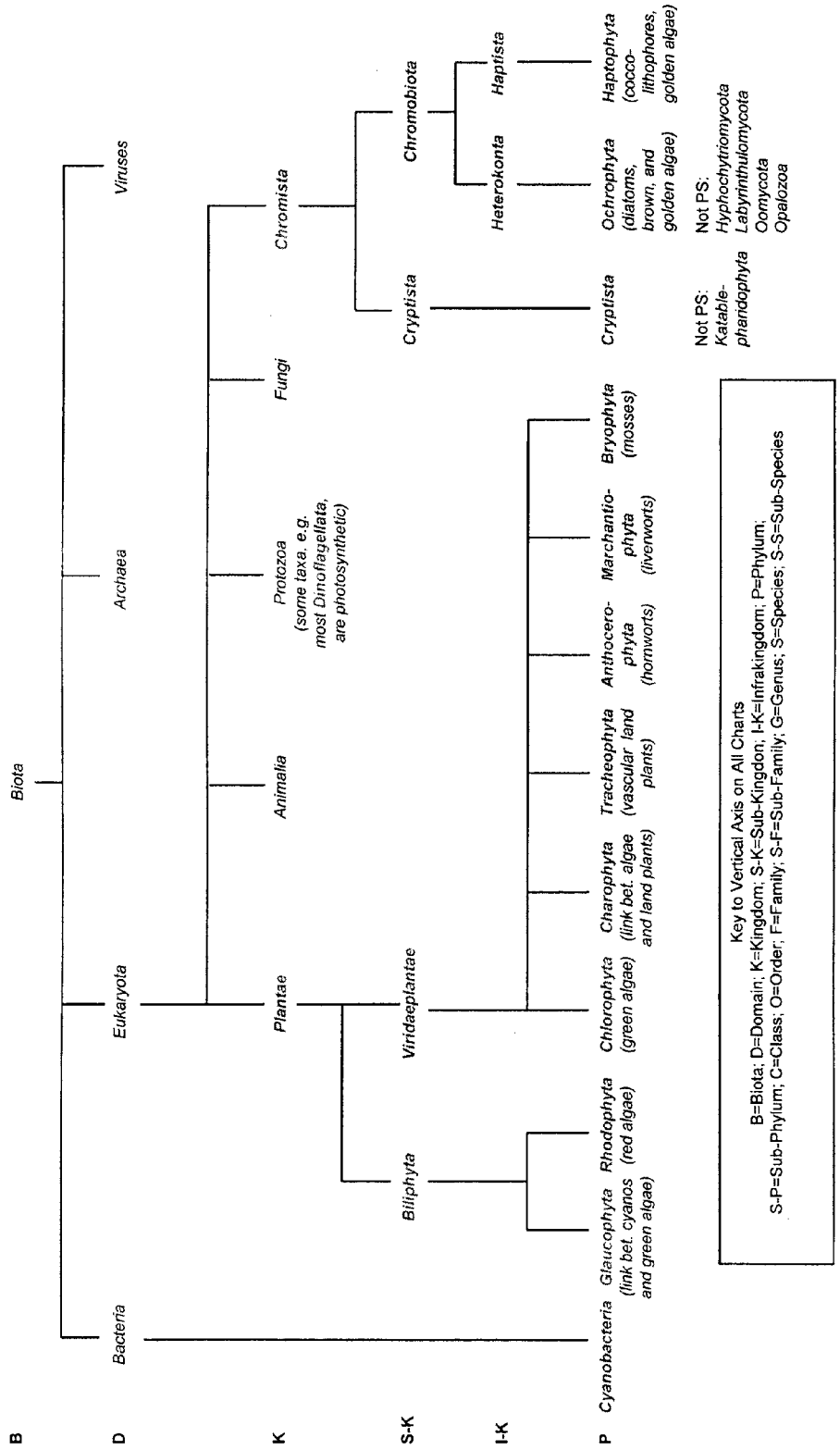
FIG. 1 shows a top level taxonomy chart of photosynthetic organisms, which may be used in certain embodiments of the present invention.

In describing and claiming the present invention, the following terminology will be used in accordance with the definitions set forth below.

The singular forms "a," "an," and "the" include plural referents unless the context clearly dictates otherwise. Thus, for example, reference to "an alga" includes reference to one or more of such algae, and reference to "the cover" includes reference to one or more of such covers.

As used herein, the term "biomass" refers to various carbon-containing materials resulting from growth of algae, cyanobacteria, and diatoms, but may include material from other growing organisms. In some aspects, a "biomass" can consist of various carbon containing materials resulting from the growth of algae, cyanobacteria, and diatoms, or even only a combination of two of these organisms. In some aspects, the term "biomass" can also include reference to only the living organisms themselves when indicated by the context used herein.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

THE INVENTION

The inventor has discovered novel and efficient techniques to achieve rapid growth of aquatic biomass. These techniques are based on observations from experimental growth of a large number of aquatic species alone and in combination with other species. Growth observations from these experiments show conclusively that certain mixed cultures grow faster than comparable monocultures.

One objective of the growth of aquatic biomass is to produce a feedstock for conversion to a biofuel. The productivity and cost of biomass production will determine the cost of the fuel, all other factors being equal. Therefore the ability to grow biomass faster and more predictably is a significant advantage for production of fuels from biomass. One factor in achieving a high biomass production is that a mix of organisms with different characteristics can be more efficient in maximizing use of available resources than a single organism or monoculture. In some mixes, different organisms may be synergistic or symbiotic, conferring yet a different kind of advantage in the mixed environment.

In particular, in an aquatic environment it is possible to grow a mix of organisms and/or species, each having a significant value as a potential fuel source, that utilize somewhat different light spectra in the photosynthetically active region of wavelengths, and that may function symbiotically to regulate depth in the water column, to process nutrients, to avoid effects such as photoinhibition, and the like. The mixture may also be more stable, and less susceptible to disease, predators, and weeds than a single species, and may further be indigenous to the growing location. By selecting and growing certain mixes of species, or organisms, the total production of biomass can be maximized with the highest growth and lowest cost.

FIG. 1 shows a taxonomical chart of primary photosynthetic organisms. The aquatic photosynthetic organisms are in one of three groups: The phylum *Cyanobacteria* in the domain *Bacteria*, various phyla of algae in the kingdom *Plantae*, and the phyla *Ochrophyta* and *Haptophyta* containing diatoms as well as certain algae in the kingdom *Chromista*. It should be noted that the exact taxonomy of some photosynthetic organisms, especially the diatoms, is not fully agreed upon in the art. The taxonomy used herein is thus shown in FIG. 1.

In one aspect, a typical healthy growth mixture can include algae, cyanobacteria, and diatoms. In such a mixture, the algae can provide much of the mass, with cyanobacteria and diatoms in descending order of mass contribution. However, these proportions are highly variable, and in some mixes the cyanobacteria or diatoms may dominate. Note however, that in some aspects, the mixture can include two organisms selected from algae, cyanobacteria, and diatoms.

The growth of these species together requires that the nutrient composition should contain everything needed by the particular species in the biomass mixture. Members of every group will most likely need the primary nutrients N—P—K (Nitrogen-Phosphorus-Potassium), as well as secondary nutrients Ca (Calcium), Mg (Magnesium) and S (Sulfur). Micronutrients are B (Boron), Cu (Copper), Fe (Iron), Cl (Chlorine), Mn (Manganese), Mo (Molybdenum), Na (Sodium), and Zn (Zinc). In addition, diatoms need Si (Silicon). The proportions may vary—for example cyanobacteria generally need more P and Mo than species in the other groups.

In addition, basic elements such as H (Hydrogen), O (Oxygen), and C (Carbon), are also required. These three elements can be derived from $CO_2$ (carbon dioxide) and $H_2O$ (water), which are broken down in the process of photosynthesis to make the basic elements available for the production of carbohydrates.

Most plants can grow and function with relatively low levels of the nutrients, but significant growth acceleration can be achieved by supplying the nutrients in more abundance. In an aqueous environment, water will be available as needed, but all other elements, including $CO_2$, can be augmented above natural levels to achieve faster growth.

Additionally, mineral elements can be supplied from either chemical or organic sources. Carbon is somewhat different, however. It can also be supplied from both chemical and organic sources, but carbon used in photosynthesis is often derived from carbon dioxide, dissolved in the water from the atmosphere. If an enriched source of carbon dioxide gas can be provided, dissolving, or otherwise mixing the gas in water to the saturation level will significantly enhance the growth rate of the biomass growing in the enriched water. Similarly, Nitrogen can also be derived from the atmosphere, but must first be "fixed", a process that cyanobacteria can provide. While cyanobacteria can thus provide N to the biomass mixture, growth can still be accelerated by adding supplemental N, thus allowing the cyanobacteria to devote more energy to biomass production and less to nitrogen fixation.

Species Selection

As will be discussed, numerous factors can influence the selection of organisms and species of organisms to be included in an aquatic biomass. Additionally, depending on how the biomass mixture of species is to be harvested, particular types may be preferable to others. For example, some species in each group are extremely small, with coccoid shapes only a few microns in diameter. These small cells can be difficult to harvest. Other species grow in long filaments, which may intertwine. These species can often be harvested more easily, for example by raking or screening. For this reason, the selection of an optimum mix can depend not just on a particular combination that grows fast, but also on ease of harvesting.

In some cases, the filamentary species that are easy to harvest are also among the most robust and fast-growing. Examples of filamentary species are abundant among both the algae and cyanobacteria. In view of the foregoing, in some aspects, the mix of algae, cyanobacteria, and diatoms may include algae and cyanobacteria that are filamentary.

One important factor includes the type of water that is present in the growing location. A species mix can be identified for any type of water—fresh water, treated wastewater, brackish or alkaline water, or saltwater. In many cases, a species that grows well in one type of water, can have a closely related species which grows well in another type of water. For example, for many freshwater species similar saltwater species can be identified.

As an example, a typical mixture of organisms and species of organisms that is robust, grows fast, is easy to harvest, and becomes dominant in a growth pond is shown in the following table.

TABLE 1

Typical Biomass Mixes

| Type | Freshwater Genus | Saltwater (Marine) Genus |
|---|---|---|
| Algae | *Cladophora* | *Ulva* |
| Cyanobacteria | *Planktothrix* | *Nodularia* |
| Diatom | *Navicula, Fragilaria* | *Nitzschia, Chaetoceros* |

Numerous organisms and species of organisms can be included in a biomass mixture depending on the desired results. As has been described, various combinations of algae, cyanobacteria, and diatoms can be utilized. It should be noted that any photosynthetic species from these groups can be included in a biomass mixture according to aspects of the present invention.

Examples of algae can include, in one aspect, without limitation, *Chara, Cladophora, Hydrodictyon, Oedegonium, Pithophora, Rhizoclonium, Spirogyra, Stigeoclonium, Ulothrix, Ascophyllum, Ulothrix*, and *Ulva*. In another aspect, examples of algae may include *Chara, Cladophora, Oedegonium, Pithophora, Spirogyra*, and *Ulva*. As another example, algae may include *Cladophora, Pithophora*, and *Ulva*.

Examples of cyanobacteria can include, in one aspect and without limitation, *Microcystis, Arthrospira, Lyngbya, Oscillatoria, Phormidium, Planktothrix, Anabaena, Aphanizomenon, Cylindrospermum, Nodularia, Nostoc*, and *Fischerella*. In another aspect, examples of cyanobacteria may include *Microcystis, Lyngbya, Oscillatoria, Planktothrix, Nodularia*, and *Nostoc*. As another example, cyanobacteria may include *Microcystis, Planktothrix*, and *Nodularia*.

Examples of diatoms can include, in one aspect and without limitation, *Amphipleura, Amphora, Biddulphia, Chaetoceros, Coscinodiscus, Cyclotella, Cymbella, Diatoma, Fragilaria, Hantzschia, Melosira, Navicula, Nitzschia, Pleurosigma, Stephanodiscus*, and *Thalassiosira*. In another example, diatoms may include *Biddulphia, Melosira, Fragilaria, Navicula, Nitzschia, Thalassiosira*, and *Chaetoceros*. As another example, diatoms may include *Fragilaria, Chaetoceros, Navicula*, and *Thalassiosira*.

Furthermore, growth of the biomass can be initiated using an initial mixture of various organisms and species of organisms in proportions to provide enhanced or synergistic growth. For example, in one aspect algae can be included in the mixture in an amount of from about 10 wt % to about 90 wt % of the initial mixture. In another aspect, algae can be included in the mixture in an amount of from about 30 wt % to about 70 wt % of the initial mixture. As another example, in one aspect cyanobacteria can be included in the mixture in an amount of from about 10 wt % to about 90 wt % of the initial mixture. In another aspect, cyanobacteria can be included in the mixture in an amount of from about 30 wt % to about 70 wt % of the initial mixture. As yet another example, in one aspect diatoms can be included in the mixture in an amount of from about 10 wt % to about 50 wt % of the initial mixture. In another aspect, diatoms can be included in the mixture in an amount of from about 10 wt % to about 30 wt % of the initial mixture.

Furthermore, the relative proportions of organisms and species of organisms can be selected for an initial mixture to provide enhanced or synergistic growth. In one aspect, for example, a two organism mixture of algae and cyanobacteria can be initiated at a weight ratio of from about 1:1 to about 6:1 In another aspect, a two organism mixture of algae and cyanobacteria can be initiated at a ratio of from about 2:1 to about 4:1. Regarding algae and diatoms, in one aspect such a two organism mixture can be initiated at a weight ratio of from about 3:1 to about 20:1. In another aspect, an algae and diatom mixture can be initiated at a ratio of from about 5:1 to about 15:1. Regarding cyanobacteria and diatoms, in one aspect such a two organism mixture can be initiated at a ratio of from about 2:1 to about 15:1. In another aspect, a cyanobacteria and diatom mixture can be initiated at a ratio of from about 3:1 to about 10:1. Additionally, various ranges of three organism mixtures can be useful. In one aspect, for example, an algae, cyanobacteria, and diatom mixture can be initiated at a ratio of from about 5:5:1 to about 10:5:1. In another aspect, an algae, cyanobacteria, and diatom mixture can be initiated at a ratio of from about 3:2:1 to about 3:4:1. In yet another aspect, an algae, cyanobacteria, and diatom mixture can be initiated at a ratio of from about 5:3:1 to about 3:5:1.

As an example, a mixture of *Cladophora, Planktothrix*, and *Navicula* can be mixed together for an initial growth mixture in the proportions of 50 wt %, 40 wt %, and 10 wt %, respectively. In another example, these three species can be mixed together for an initial growth mixture in the proportions of 60 wt %, 35 wt %, and 5 wt %, respectively.

As has been described, a variety of factors can contribute to the preselection and incorporation of various organisms and species into a biomass. Non-limiting examples of such factors include wavelengths of light used, buoyancy, temperature, nutrient use, culture stability, and predator control. These factors are discussed below.

Wavelength

The wavelengths of light utilized by the aquatic biomass as a whole affect the overall quantum efficiency of the total biomass mixture. One particular organism or species can utilize a particular range of wavelengths, while a different organism or species can utilize other wavelengths. Even though the range of wavelengths will likely involve some overlap among organisms and species, the aquatic biomass as a whole will photosynthesize across a wider region of the light spectrum as compared to a monoculture of a single species.

As an example, a species of green algae may absorb primarily red and blue wavelengths of light, and reflect yellow and green wavelengths, thus giving the algae its characteristic green or yellow-green color. A species of cyanobacteria may use somewhat more of the red and yellow spectrum, reflecting more blue and green, giving the growth a characteristic blue-green color. Diatoms may appear golden, reddish, or brown, because the diatoms reflect relatively more oranges and reds and absorb relatively more yellow-greens and blues. These differences are the result of different pigments in the harvesting structures of the different species, or in the case of diatoms, the mechanical structure of the frustule (cell wall) can cause a diffraction and/or waveguide effect which preferentially selects certain wavelengths. Such a diffraction and/or waveguide effect is in addition to harvesting pigments in diatoms.

Accordingly, a carefully selected mix of species can utilize a wider range of light wavelengths, thus absorbing and converting more of the total photon flux incident on the total growth. As a result more of the incident sunlight is used and less is wasted, allowing higher total growth per unit of growing area and per unit of time.

Another benefit to the utilization of a larger portion of the incident photon flux by an aquatic biomass is the reduction of photoinhibition that can occur in photosynthetic organisms. Photoinhibition is a phenomenon whereby the photosynthetic mechanism of an organism is inhibited or damaged by a photon flux in excess of what the organism can utilize. In a biomass mixture as has been described herein, photoinhibition can be reduced because wavelengths of light that would normally cause inhibition in a particular organism are utilized by other organisms in the mixture. Thus the greater the range of absorption of light by the biomass mixture, the less photoinhibition is caused by unused wavelengths of light.

Table 2 shows more detailed examples pigments present in various photosynthetic organisms, showing the color of the pigment and the organisms where it is most commonly found.

TABLE 2

Common Photosynthetic Pigments

| PIGMENT | TYPE | COLOR (Unabsorbed Wavelengths) | AQUATIC PHOTOSYNTHETIC ORGANISMS |
| --- | --- | --- | --- |
| Allophycocyanin | Phycobiliprotein | Purple | Cyanobacteria, red algae |
| Antheraxanthin | Xanthophyll | Yellow or Cream | Algae, red algae, cyanobacteria |
| Apocarotenal | Carotene | Orange or Orange-red | Green algae |
| Astaxanthin | Xanthophyll | Red | Green algae, esp. *Haematococcus* |
| Canthaxanthin | Xanthophyll | Pink | Green algae |
| α-Carotene | Carotene | Orange | Green algae |
| β-Carotene | Carotene | Orange | Green algae |
| ε-Carotene | Carotene | Orange | Green algae |
| γ-Carotene | Carotene | Orange | Green algae |
| τ-Carotene | Carotene | Orange | Green algae |
| Chlorophyll a | Primary photosynthetic molecule | Yellow-green | All |
| Chlorophyll b | Chlorophyll accessory pigment | Blue-green | Green algae |
| Chlorophyll c | Chlorophyll accessory pigment | Green | Diatoms, dinoflagellates, brown algae |
| Chlorophyll d | Chlorophyll accessory pigment | Green | Certain cyanobacteria, red algae |
| Chlorophyll e | Chlorophyll accessory pigment | Green | Several algae |
| Diadinoxanthin | Xanthophyll | Yellow | Diatoms, dinoflagellates |
| Diatoxanthin | Xanthophyll | Yellow | Diatoms |
| Dinoxanthin | Xanthophyll | Yellow | Dinoflagellates |
| Flavoxanthin | Xanthophyll | Orange | Diatoms, dinoflagellates, brown algae |
| Fucoxanthin | Xanthophyll | Yellow | Diatoms, brown algae |
| Lutein | Xanthophyll | Yellow | Diatoms, brown algae, dinoflagellates |
| Lycopene | Carotene | Red | Algae, cyanobacteria, diatoms |
| Neoxanthin | Xanthophyll | Yellow | Green algae, brown algae |
| Peridinin | Xanthophyll | Yellow | Dinoflagellates |
| Phycocyanin | Phycobiliprotein | Blue | Cyanobacteria, red algae |
| Phycoerythrin | Phycobiliprotein | Red/brown | Cyanobacteria, red algae |
| Phycourobilin | Phycobiliprotein | Orange | Cyanobacteria, red algae |
| Violaxanthin | Xanthophyll | Orange | Algae, red algae, cyanobacteria |
| Zeaxanthin | Xanthophyll | Yellow | Algae, red algae, cyanobacteria |

Buoyancy

The ability to control buoyancy allows an aquatic organism to regulate its vertical position (depth) in the water column, which may be a significant advantage in achieving rapid growth. The depth may affect various factors such as the amount and color of sunlight that penetrates and reaches the organism, the ability to select for different temperatures of the water at different depths, the amount and type of nutrients and dissolved gases, currents and movement of water, and the ability to avoid excess solar radiation which can cause photoinhibition.

Buoyancy regulation is more common in cyanobacteria than in algae or diatoms. This is one of the reasons why cyanobacteria can sometimes totally dominate the aquatic environment by forming dense "blooms". Cyanobacteria accomplish buoyancy regulation by the use of gas vesicles and by changes in their storage polymer contents, capabilities which may be absent in the other species. In a mixture of species in an aquatic biomass, cyanobacteria can provide buoyancy effects to the entire biomass mixture, since the species are often rather tightly intertwined due to the filamentary nature of certain species in the mixture. At the very least, species with the ability to regulate buoyancy may be able to continue to grow as temperatures change, contributing some biomass growth even when non-regulating species have almost or completely stopped growing.

Temperature

A variety of growth conditions can be used to further provide enhanced growth of the biomass mixture. For example, a biomass mixture can be selected for growth at a particular temperature, or a temperature can be provided to enhance the growth of a particular biomass mixture. Certain species can grow more effectively at some temperatures as compared to others. Thus by providing optimal temperature to the biomass mixture, growth can be enhanced. Additionally, a buoyancy regulating species can regulate the depth of the biomass in a growth environment to a water level where temperatures are more effective for growth.

Although the temperature at which the biomass is grown can vary depending on the makeup of the biomass, in one aspect the water temperature can be from about 5° C. to about 40° C. In another aspect the water temperature can be from about 10° C. to about 35° C. In yet another aspect the water temperature can be from about 15° C. to about 30° C.

The combination of species selected for the biomass mixture and the growth conditions under which the biomass is grown can have an enhancing or a synergistic effect on the growth of the biomass. For example, in one aspect, the growth rate of a biomass mixture can be from about 10% to about 90% greater than the growth of monocultures of each of the biomass constituents under comparable growth conditions. In another aspect, the growth rate of a biomass mixture can be from about 30% to about 70% greater than the growth of monocultures of each of the biomass constituents under comparable growth conditions.

Nutrient Use

Similar to the ability of different organisms and species to utilize different wavelengths of light, so can they also make use of different nutrients, or different concentrations of nutrients. One example is the ability of cyanobacteria to fix nitrogen—that is, to convert the dinitrogen molecule to a biologically available form such as ammonia or nitrates. Cyanobacteria are generally capable of fixing more nitrogen than they need, and the excess is then available to other plants in their vicinity. In the case of aquatic biomass, the presence of cyanobacteria can provide nitrogen to the other members of the mix—the algae and diatoms.

To grow a biomass at the highest possible rate, nutrients can be supplied in the optimum concentration, which will also include nitrogen. However, as a cost reduction, cyanobacteria can provide at least some of the nitrogen that would otherwise be provided by external means.

Relative to the other species mentioned, cyanobacteria also tend to favor higher concentrations of phosphorus and molybdenum. Diatoms need silicon to form the silica cell walls of the frustule.

In short, a mix of species can make optimum use of a wider range of primary, secondary, and micro-nutrients. As with the ability of a mix of species to use a wider range of light, the ability to use a wider range of nutrients can enhance total production.

Stability of Culture

Monocultures can be difficult to maintain, both in terms of the health of the single species, and in terms of protection from invasion by predators or undesired species ("weeds"). It is well known that monocultures can sometimes "crash" when the growth system becomes unbalanced, and in some instances the entire growth is lost. Crashes are more prevalent in closed growth systems such as pipes or other photobioreactors, but they can and do occur in open or outdoors systems as well.

One cause of monoculture crashes is viral infection. It is known that many species of algae are susceptible to viral attack. The targeting by the virus can be exquisitely precise, such that a particular virus attacks only a single species or sub-species of algae, and no other. It is thought that for every alga there may be a virus which targets it, but given the sheer number of algae species and sub-species, this theory, while logical, is unproven. Research has also demonstrated viral infections in cyanobacteria and diatoms.

Clearly, if a monoculture of any single species is attacked by a virus that targets that particular species, the entire growth can be lost. A viral crash happens very quickly, often in just a few hours. Occasionally the virus can be controlled by chemical or pharmaceutical means, but in general the only recovery is to completely drain the growth medium, start with new water, and re-seed the culture.

In a monoculture, similar attacks can take place by invasive species, such as predators or weeds. While an invading species will not usually kill the desired culture as a virus attack does, it can nevertheless reduce the yield of the crop, and also complicate the harvesting of the crop. Over time the weeds may come to dominate the culture. The solution is often to keep a separate culture of the desired species in a controlled environment, and re-seed the larger growth on a regular basis to help maintain dominance over the weeds. While workable, this solution adds extra cost.

By comparison, a mixed culture is less susceptible to crashes and to being taken over by invaders. Mixed cultures have been found to be more resistant overall to viral attacks, and even if one species in a mix is attacked, the others will not be susceptible to that particular virus and will not be harmed. In addition, once a healthy mixed culture is established, it tends to become dominant and use all available resources. Invaders have far more difficulty in finding a niche and getting established than they would in a monoculture.

Predator Control

All of the species described as candidates for the biomass-growth mix have predators or grazers in addition to the viruses described above. One of the significant advantages of having cyanobacteria in the mix is that some species of cyanobacteria can inhibit the growth of predators. For example, some dinoflagellates, a kind of protozoa, may prey on diatoms, but are discouraged by substances produced by cyanobacteria. These interactions are not well understood, but may be another component of the greater success and growth rates of mixed species.

EXAMPLES

Example 1

Growth System

The growth structure may be either open shallow ponds or a series of troughs approximately 2 m wide, 100 m long, and 40 cm deep built directly into the earth. The troughs contain approximately 30 cm of water. The troughs may be open or may be covered with plastic film that is perforated to allow gas exchange. The covers reduce evaporation and improve temperature control in the water.

The water in the troughs is supplemented with nutrients needed for rapid growth, consisting of nitrogen, phosphorus, potassium, as well as secondary and trace elements. The troughs have a means to introduce nutrients, as well as carbon dioxide either from the atmosphere or from supplemental sources.

The initial organisms grown in the ponds or troughs are a mixture of *Cladophora* (algae), *Planktothrix* (cyanobacteria), and *Navicula* (diatom). The proportions of the mixture will adjust over time naturally, but will generally be more than 50% algae, with the remainder being cyanobacteria and diatoms.

The growing organisms are harvested continually by removing a portion of the biomass, by raking or similar gathering, or by use of a weir or seine.

The biomass is processed further to remove a portion of the water and undesirable objects. For example, the biomass may be processed to remove sticks, stones, and sand. It may then be milled to yield a smooth mix and stored in feed tanks as a slurry. This slurry will be used in the fuel production apparatus.

Example 2

Species Selection Procedure

Selection of species for each mixture component can be determined on a custom basis for the selected production environment in which the mixed biomass is to be grown. Single-species for each mixture component are grown in covered containers and the growth rates (dry mass produced per unit of time and volume) are recorded. All conditions should be maintained identically from test to test, including temperature, light intensity, nutrients supplied, air or carbon dioxide supply, etc., and matched to the production environment as closely as possible. The most fruitful species from each component (i.e. algae, cyannobacteria, and diatoms) is then selected to be used in the production mixture. This process is also performed with mixtures of species for each component when multiple species are to be used in each component of the production mixture. For example, two or three species of algae, two species of diatoms, and one species of cyannobacteria can be cultivated and selected for the production mixture.

Example 3

Mixed Growth Testing

The test consists of seven small rectangular open tanks with dimensions 350 mm×300 mm×125 mm deep. 10 L of water is placed in each tank. A measured amount of nutrient mix consisting of primary nutrients (nitrogen, phosphorus, potassium), micronutrients (including silicon for the diatoms), and vitamins is added to each tank. The tanks are placed on a laboratory bench with a large window the length of the bench. All tanks have a uniform overhead lighting system as well, but it provides less light than the window during daylight hours Ambient temperature in the laboratory is 23° C. Three tanks are inoculated with 15 g dry weight of material. Tank 1 receives *Cladophora*, a filamentous alga. Tank 2 receives *Planktothrix*, a cyanobacterium, and Tank 3 receives *Cocconeis*, a diatom. Tanks 4, 5, and 6 receive two sets of material each, with the combinations *Cladophora-Planktothrix*, *Cladophora-Cocconeis*, and *Planktothrix-Cocconeis*. Tank 7 receives three sets of material, one of each type.

Once per week the tanks are refilled to a mark indicating the 10 L level with water that has been allowed to reach ambient temperature in the laboratory. A uniform measured amount of nutrient mix is added at the same time. The water is stirred gently but sufficiently to achieve a uniform mix in each tank, and then a measured sample of 10 mL is taken from each tank. The sample is evaporated and dried, then weighed. The experiment runs for three months, and a final sample is taken from each tank.

An analysis of the data taken at the final sample shows that the desired growth enhancement has occurred. The expected advantage of faster growth is achieved by all the mixtures compared to any single-species growth. The mixture of all three achieves nearly 50% greater final dry weight than any of the single-species growths. The mixtures of *Cladophora-Planktothrix* and *Cladophora-Cocconeis* achieve app. 30% greater dry mass than any single-species tank, and the mixture of *Planktothrix-Cocconeis* app. 20% greater dry mass. *Cladophora-Cocconeis* is especially interesting, as the *Cocconeis* forms a slippery coating all over the *Cladophora*.

In addition the mixtures show a slight tendency toward browning or yellowing compared to the single-species tanks, especially the ones identified as the fastest-growing. This means that the faster growth is depleting the nutrients faster, as would be expected. In practice the nutrient additions would be increased for the mixes above any single-species level to avoid nutrient depletion.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of enhancing growth of an aquatic biomass, comprising:
    preselecting a combination of aquatic biomass constituents including at least two organisms selected from the group consisting of an algae mixture, a cyanobacteria mixture, and a diatom mixture, wherein the aquatic biomass constituents provides the aquatic biomass with buoyancy control, a photoabsorption capacity in a spectrum of 350 nm to 750 nm in wavelength that is about 30% to about 70% greater than any single biomass constituent, and a degree of photoinhibition in the 350 nm to 750 nm wavelength spectrum that is about 30% to about 70% less than a single biomass constituent; combining the aquatic biomass constituents at a growth accelerating ratio; wherein the ratio of algae to cyanobacteria is from about 1:1 to about 6:1 and the ratio of algae to diatoms is from about 3:1 to about 20:1 and the ratio of cyanoabacteria to diatoms is from about 2:1 to about 15:1; and growing the combination of aquatic biomass constituents in natural sunlight and at a temperature range of from about 10° C. to about 35° C.

2. An aquatic biomass with accelerated growth capacity comprising:
    a preselected combination of aquatic biomass constituents including at least two organisms selected from the group consisting of an algae mixture, a cyanobacteria mixture and a diatom mixture, wherein the aquatic biomass constituents provides the aquatic biomass with buoyancy control, a photoabsorption capacity in a spectrum of 350 nm to 750 nm in wavelength that is about 30% to about 70% greater than a single biomass constituent, and a degree of photoinhibition in the 350 nm to 750 nm wavelength spectrum that is about 30% to about 70% less than a single biomass constituent; wherein the ratio of algae to cyanobacteria is from about 1:1 to about 6:1 and the ratio of algae to diatoms is from about 3:1 to about 20:1 and the ratio of cyanoabacteria to diatoms is from about 2:1 to about 15:1.

3. The aquatic biomass of claim 2, wherein at least one of the organisms includes at least two species of organisms.

4. The aquatic biomass of claim 2, wherein the at least two organisms includes three organisms including at least one alga, at least one cyanobacterium, and at least one diatom.

5. The method of claim 1, wherein the combination of biomass constituents includes three organisms including at least one alga, at least one cyanobacterium, and at least one diatom.

6. The method of claim 1, wherein one of the at least two biomass constituents is an algae, and wherein the algae is filamentary.

7. The method of claim 1, wherein one of the at least two biomass constituents is an algae, and wherein the algae is from the genus *Cladophora*.

8. The method of claim 1, wherein one of the at least two biomass constituents is an algae, and wherein the algae is from the genus *Ulva*.

9. The method of claim 1, wherein one of the at least two biomass constituents is a cyanobacterium, and wherein the cyanobacterium is filamentary.

10. The method of claim 1, wherein one of the at least two biomass constituents is a cyanobacterium, and wherein the cyanobacterium is from the genus *Planktothrix*.

11. The method of claim 1, wherein one of the at least two biomass constituents is a cyanobacterium, and wherein the cyanobacterium is from the genus *Nodularia*.

12. The method of claim 1, wherein one of the at least two biomass constituents is a diatom, and wherein the diatom is from the genus *Navicula*.

13. The method of claim 1, wherein one of the at least two biomass constituents is a diatom, and wherein the diatom is from the genus *Nitzschia*.

14. The method of claim 1, wherein the at least two biomass constituents includes an algae and a cyanobacterium.

15. The method of claim 1, wherein the at least two biomass constituents includes an algae and a diatom.

16. The method of claim 1, wherein the at least two biomass constituents includes a cyanobacterium and a diatom.

17. The method of claim 1, wherein the step of growing takes place in a growth environment that is a freshwater aquatic environment.

18. The method of claim 1, wherein the step of growing takes place in a growth environment that is a saltwater aquatic environment.

* * * * *